Feb. 5, 1974 L. H. SHOESMITH Plant Pat. 3,463
CHRYSANTHEMUM PLANT (MAGICIAN)
Filed May 30, 1972
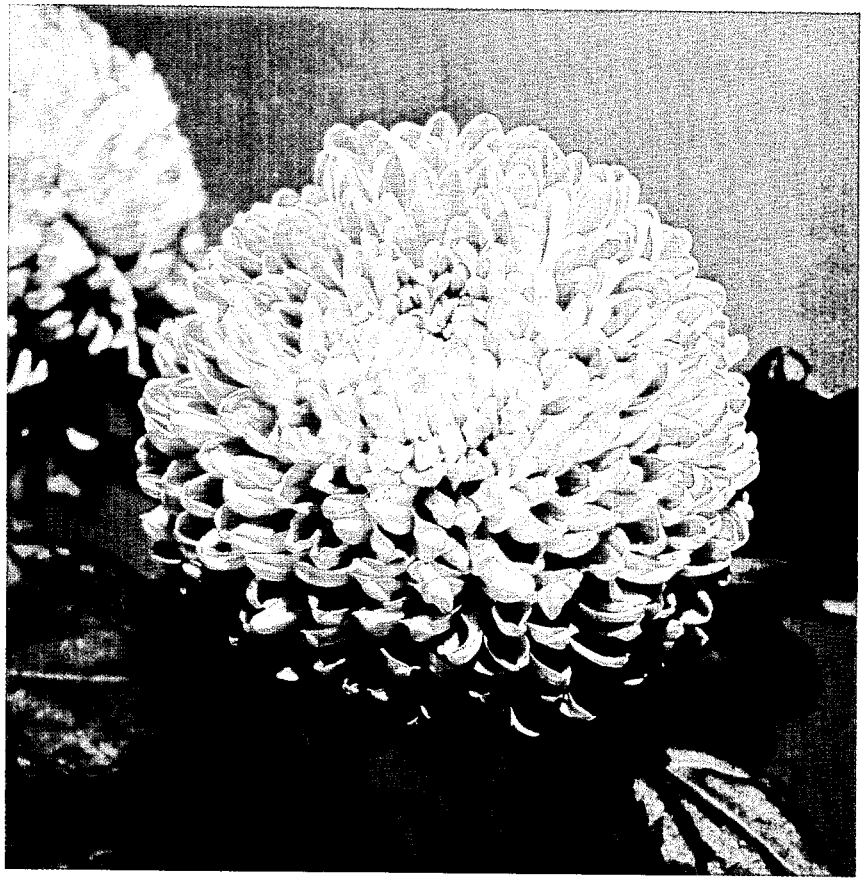
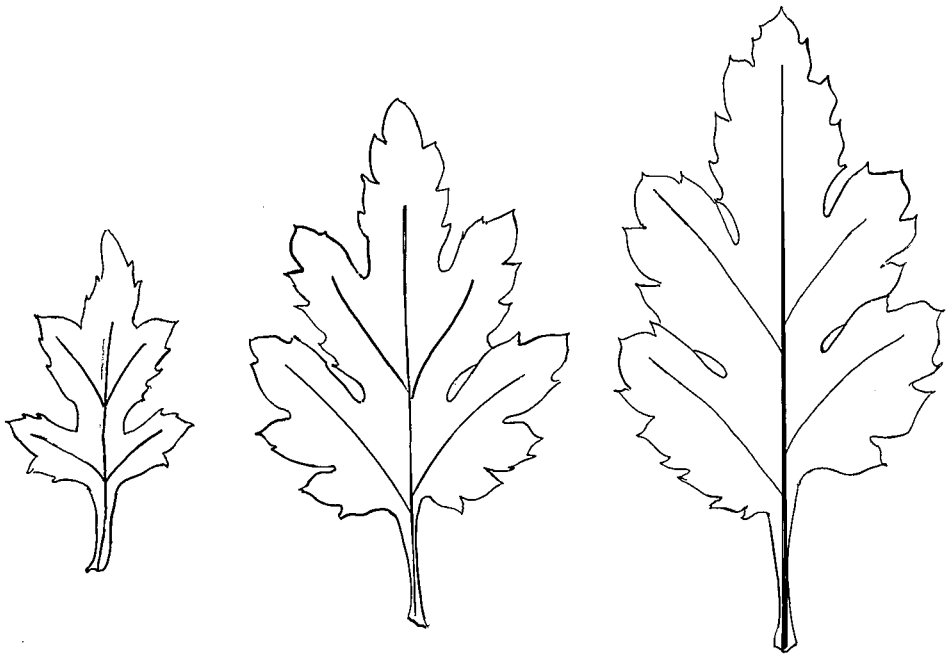

United States Patent Office

Plant Pat. 3,463

Patented Feb. 5, 1974

3,463

CHRYSANTHEMUM PLANT

Leonard H. Shoesmith, Westfield-Woking, England, assignor to Pan-American Plant Company, Chicago, Ill.

Filed May 30, 1972, Ser. No. 258,004

Int. Cl. A01h *5/00*

U.S. Cl. Plt.—79 1 Claim

ABSTRACT OF THE DISCLOSURE

A new variety of *Chrysanthemum morifolium* of standard incurved type for greenhouse culture having a nine-week response and producing very large, long lasting, golden apricot-bronze flower heads. This plant is a sturdy and vigorous grower with abundant foliage and is most suited for spring and fall flowering in northern states and for flowering from October through March in the southern states.

BACKGROUND OF THE NEW PLANT

This new variety of chrysanthemum plant was discovered by me as a seedling of unknown parentage growing among a stock of greenhouse plants maintained for use in an extensive breeding program being carried on for the purpose of producing new chrystanthemum varieties having improved characteristics of growth, strength, response, and size and color of flowers. This plant was noted in November 1968 for the large size and and beautiful color of its bloom and asexual propagation of the plant, by cuttings, under my direction at West Chicago, Ill., has demonstrated the plant to have other extraordinary and advantageous characteristics which make it a valuable addition to the commercial chrysanthemum line. Continued asexual propagation of this new plant at West Chicago, Ill., and at Cortez, Fla., has demonstrated conclusively that the distinctive characteristics of the plant are fixed and hold true from generation to generation.

DESCRIPTION OF THE DRAWING

My new variety of chrysanthemum plant is illustrated by the accompanying drawing which shows the form and color characteristics of the flower, as nearly true as is reasonably possible by means of conventional photographic procedures, and which shows by pen and ink drawings the configuration of typical specimens of the leaves.

DESCRIPTION OF THE NEW PLANT

The following is a detailed description of my new variety of chrysanthemum plant with the color designations according to the Horticulural Colour Chart produced by Robert F. Wilson and issued by The British Colour Council in collaboration with the Royal Horticultural Society.

*The plant*

Origin: Seedling
Parentage: Unknown
Classification:
- Botanic—*Chrysanthemum morifolium*
- Commercial—standard incurved Form: Perennial herbaceous bush
Height: About 4 feet
Growth: Terminal. Vigorous, sturdy and upright, with good strength
Branching: Branching occurs under natural conditions
Foliage: Abundant—36 leaves on 3 feet of stem
- *Leaf size.*—Mature leaf—5 inches long x 3½ inches wide
- *Shape.*—Lobed and slightly serrated
- *Texture.*—Canescent

- *Color.*—Upper side—Parsley green 00962. Under side—Spinach Green 0960/3
- *Venation.*—Pinnately veined
- *Petioles.*—1½ inches long Recommended only for greenhouse culture.

*The bud*

Form: Globular
Size: Diameter—1½ inches. Depth—½ inch
Opening rate: Bud opens slowly. 4 weeks to full size of flower
Color: When florets begin to unfurl—Sulfur Yellow 1/2 streaked with Spanish Orange 010/1
Phyllaries: The outer side of the receptacle bears many involucral bracts that are distinct. They stand up and are spear shaped
- *Color.*—Inside—Spinach Green 0960/2. Outside—Spinach Green 0960/3
- *Surface texture.*—Canescent Calyx: Represented by tiny bristles arising from the top of the ovary, or it may be absent
Peduncle: Erect and 3 to 4 inches long
- *Surface texture.*—Canescent
- *Color.*—Spinach Green 0960/3

*The flower*

Response: Nine weeks
Recommended flowering: May through October
Natural flowering season: End of October
Blooms: Flower type—standard incurved
- *Size.*—Very large. Diameter—5 to 5½ inches. Dept—3½ to 4 inches
- *Borne.*—One head of many florets borne on a receptacle
- *Shape.*—Flat and round when bloom first opens, becoming more globular as the florets develop
- *Florets.*—Number—numerous. Form: Linear with obtuse apex. Color: Inner and upper surface—Burnt Orange 014 streaked with Sulfur Yellow 1/1 and with base of Chartreuse Green 663/1. Reverse side—Sulfur Yellow 1/2. Firmness: Medium. Appearance: Velvety. Discoloration: None
- *Peduncle.*—Upright, sturdy and erect—3 to 4 inches long. Color: Spinach Green 0960/2

Persistence: Florets hang on and dry
Fragrance: None
Lasting quality: On plant—3 to 4 weeks. As cut flower—2 weeks

*Reproductive organs*

Stamens:
- *Filaments.*—5, syngeneiously arranged. Length: ¼ inch. Color: Yellow
- *Anthers.*—Connate to form a cylinder about the style.
- *Pollen.*—Color—Yellow Pistils:
- *Number.*—One for each ray floret
- *Style.*—Length—5/16 inch
- *Stigmas.*—Color—Straw Yellow Characteristics of ovaries: Inferior—Thicarpellate and sterile The principal distinction of this new variety of chrysanthemum resides in the golden apricot-bronze coloring of the outer surfaces of the florets which combines with a lighter golden color of the reverse surfaces to provide a very striking and beautiful flower. This variety most nearly resembles Improved Detroit News (unpatented) but holds its color better and has a larger, deeper and more incurved flower form. This new variety is also a more rapid grower and reaches a height from 12 to 14 inches taller than Improved Detroit News.

I claim:

1. A new and distinct variety of chrystanthemum plant, substantially as herein shown and described, characterized by its vigorous and rapid growth habit, its consistent 9 week response to photoperiod culture, and the generally golden brown color of its very large globular flowers.

No references cited.

ROBERT E. BAGWILL, Primary Examiner